United States Patent [19]

Wettermann et al.

[11] 4,155,452

[45] May 22, 1979

[54] INTERLOCKING STACKABLE HOUSING STRUCTURE

[75] Inventors: Ludwig A. Wettermann, Arlington Heights; William F. Auer, Des Plaines, both of Ill.

[73] Assignee: Richard Wolf Medical Instruments Corporation, Rosemont, Ill.

[21] Appl. No.: 867,717

[22] Filed: Jan. 9, 1978

[51] Int. Cl.² .............................................. B65D 21/02
[52] U.S. Cl. ..................................... 206/512; 206/821; 312/211
[58] Field of Search .................... 206/511, 512, 821; 312/211

[56] References Cited

U.S. PATENT DOCUMENTS

| | | | |
|---|---|---|---|
| 1,010,801 | 12/1911 | Rapp | 206/511 |
| 1,038,923 | 9/1912 | Mathy | 206/511 |
| 1,331,862 | 2/1920 | Claus | 312/111 |
| 2,404,777 | 7/1946 | Gaines | 220/69 |
| 3,159,436 | 12/1964 | Davis | 206/511 |

FOREIGN PATENT DOCUMENTS 940098  3/1956  Fed. Rep. of Germany ........... 206/821

Primary Examiner—George E. Lowrance
Attorney, Agent, or Firm—Kinzer, Plyer, Dorn & McEachran

[57] ABSTRACT

A surgical accessory equipment housing having mounting pads at the lower corners which permit stacking of a plurality of such housings by serving as a non-slip support for the bottom housing and as an interlocked spacer between the stacked housings. Each pad has a right angular foot which engages the upper corner of a subjacent housing with spacer ribs disposed between the housings. The bottom housing rests on a flat surface, supported by the four feet of its mounting pads.

9 Claims, 5 Drawing Figures

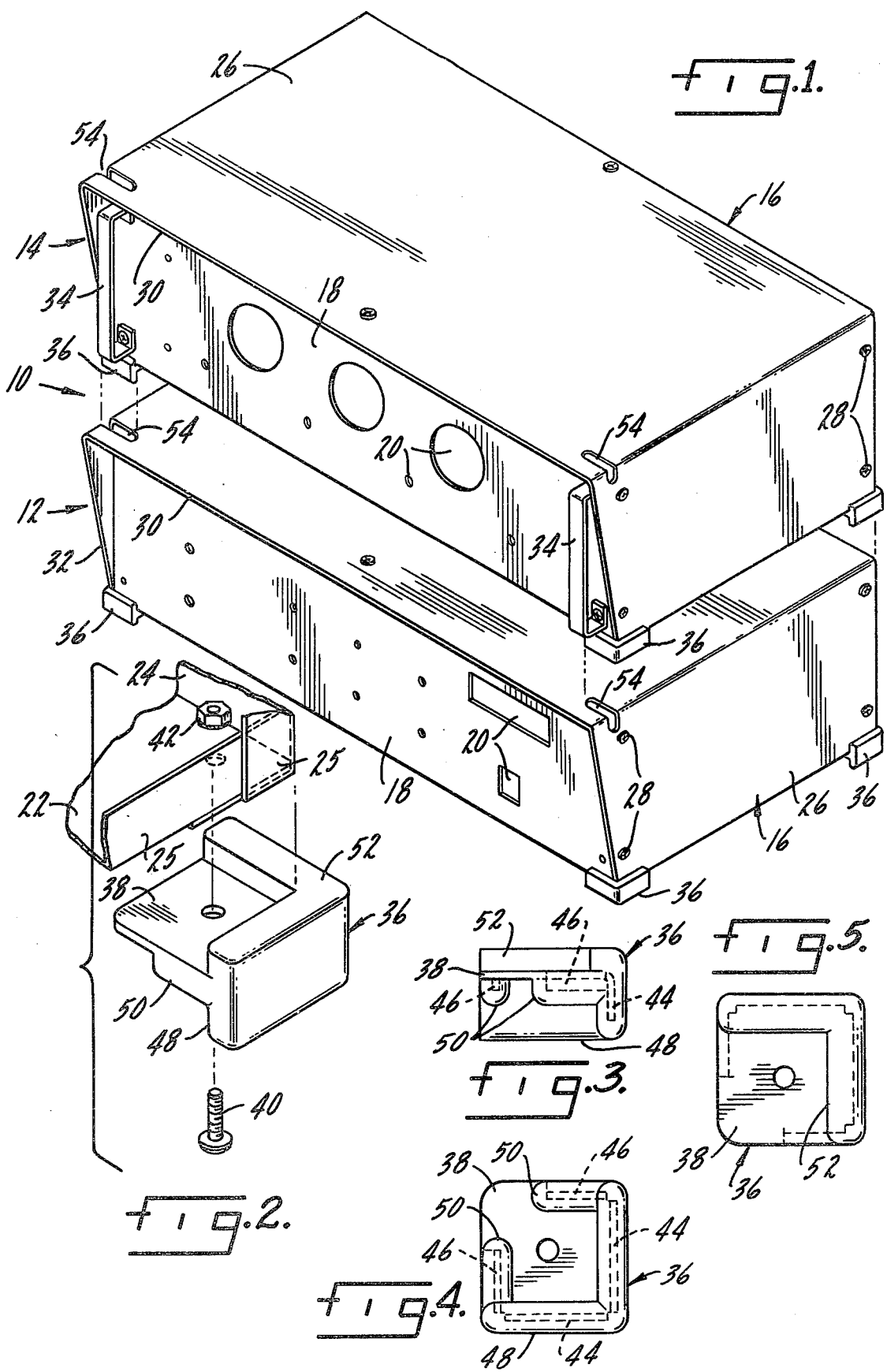

INTERLOCKING STACKABLE HOUSING STRUCTURE

This invention relates to surgical equipment and in particular to housings for that equipment so constructed as to be interfittable one with another in a stack.

Some forms of surgery, particularly on the abdomen and within the urinary tract, are aided by sophisticated, unitized equipment including insufflators for introducing $CO_2$ into the abdomen (to distend the internal organs), high energy sources for electrosurgical instruments employed in resection and coagulation, fiber optic light sources for endoscopy, and so on.

The units, when made separately and confined in separate housings, are usually allocated to separate stands or shelves in the operating room. This may require repeated handling of each unit but more worrisome is the plain fact that there may be too much crowding.

It has been proposed to combine several of the functional units in a single, "duplex" housing. There are two difficulties with that.

One difficulty is that the units themselves are expensive, meaning the manufacturer has an expensive inventory to maintain. This problem is exacerbated when a hospital may find itself duplicating an existing function in order to acquire a new one incorporated in the "duplex" housing. The hospital can acquire the new function only along with the one already available at the hospital. Also, if only one of the units in the "duplex" housing requires servicing both functions become unavailable if the housing has to be removed from the operating room.

The other difficulty with combined units is the hospital may more often than not need prompt action when it comes to servicing. Expedited transportation is required, even air express sometimes, but both public and private express services place a limit on the weight they will handle. Combined units are apt to exceed such limits.

The object of the present invention is to overcome the difficulties just mentioned by constructing separate housings for the individual functions, that may be easily stacked atop one another in an interlock relation without apprehension of relative displacement. Specifically an object of the present invention is to construct symmetrical housings, housing the functional equipment required in the operating room, so that the four lower corners of an upper housing may be anchored to the four upper corners of a subjacent housing, while at the same time assuring the bottom housing will stay in place when set on a table serving as a support for the housings.

IN THE DRAWINGS

FIG. 1 is a perspective view of two housings, one atop another, constructed in accordance with the present invention;

FIG. 2 is a fragmentary perspective view showing one way of securing a supporting pad to the housing;

FIGS. 3, 4 and 5 are elevation and plan views of the foot or pad structure.

DESCRIPTION OF THE PREFERRED EMBODIMENT

FIG. 1 shows an exploded view of a stack 10 of two surgical accessory housings. These housings enclose equipment of the type described above. For example, the bottom unit 12 could be a high energy generator for electrosurgery while the top unit 14 could be insufflation equipment. The stack is designed to accommodate a third or even a fourth unit if necessary, but for convenience these are not shown as the invention can be described by the two-unit stack. The position of the units in the stack is not critical. The mounting pad of this invention permits stacking them in any desired order.

Each surgical accessory unit has a housing 16 which is generally of the shape of a rectangular box or parallelepiped. The housing is formed by joining together appropriately-sized metal stampings. The instrument panel 18 is at the front of the housing and has a series of apertures 20 for receiving the switches, dials and gauges of the particular unit. These switches and dials are not shown in the drawing. As seen in FIG. 2, the bottom panel 22 and back panel 24 have their edges folded to form flanges 25 which provide joining surfaces for fitting the panels together. This can be done by spot welding or other suitable means. The instrument panel 18 is similarly connected to the bottom panel. A one-piece cover 26 presents the top and side walls of the housing. The cover is attached to the bottom, back and instrument panels by screws 28. This configuration provides three-sided access to the inside of the unit should servicing be required.

The cover 26 does not make a square, flush corner at the upper edge of the instrument panel 18. Rather, the cover extends forwardly beyond the plane of the front panel to form a projecting hood 30. The side panels of the cover are angled at the front edge so that the extension of the cover beyond the face of the instrument panel gradually decreases from the top edge toward the bottom. At the bottom corners the side panels are flush with the instrument panel 18. This is best seen in the bottom unit 12 at 32.

Ordinarily, in an operating room, the electrosurgery and insufflation equipment is set on a tilted table so that the dials are easily viewed. The tilting puts the instrument panel in line with the surgeon's line of sight. The hood 30 helps make the dials easier to read as it tends to lessen the glare on the instrument panel. The hood also serves as a convenient lifting point when a unit is placed onto or removed from the stack. Carrying handles 34 are provided at the front of the unit (not shown in the bottom unit 12). There is also a handle on the back panel 24 (also not shown).

The lower corners of each housing have fitted thereto pads or feet 36. The pads at each of the four corners are all alike. Each pad comprises a metal plate 38 engaged with the bottom panel 22. The connection between the pad and housing can be made by a bolt 40 and nut 42 combination as shown in FIG. 2 or with a self-tapping screw.

The details of the pad construction can be seen in FIGS. 3, 4 and 5. On the underside of the metal plate 38 are downwardly directed reinforcing lugs. Two of these lugs 44 extend along the length of adjacent sides of the metal plate. At the ends of these lugs are shorter lugs 46 extending along the other two sides of the plate 38. An elastomer is molded over both the long lugs 44 and the shorter ones 46. So covered, the long lugs 44 form a continuous right angular foot 48 at the bottom of the plate 38. The short lugs 46, which only extend about half the distance from the plate as do the long lugs 44, become, when covered, spacer ribs 50 at the underside of the plate. On the upper side of the plate, which fits against the bottom panel 22, the molded elastomer extends to form a right angular guide 52 which embraces the corner of the housing.

The pads on the bottom unit 12 serve as nonslip supports for the stack 10. As can be seen in FIG. 3, the stack rests on the right angular foot 48 of each of the four pads.

The housing of the upper unit rests on the spacer ribs 50 of the pads. This is because the right angular foot is so located as to fit around the corner of the subjacent unit rather than on it. It can be seen that since the guide 52 encloses the lower corner of the housing, the right angular foot 48 will also envelop the corner of the like-sized housing of the lower unit. Slots 54 are cut in the hood 30 to provide clearance for the portion of the right angular foot 48 that would otherwise contact the hood. The upper units then rest on the spacer ribs 50 with the right angular feet 48 embracing the corners of the subjacent unit to provide an interlocked support between the units.

We claim:

1. A box-like surgical accessory housing comprising a top wall, side walls, a bottom wall, a back wall and a front instrument panel having openings therein for instruments employed in the course of surgery, and the four corners at the bottom of the housing each having attached thereto a support pad comprising:
   (a) a plate engaged with the bottom wall;
   (b) said plate having a downwardly directed first reinforcement along at least one of the plate edges parallel to the local edges of the bottom wall and said plate further having a second downwardly directed reinforcement opposed to the first reinforcement;
   (c) an elastomer molded to said first and second reinforcements to afford both a foot at the bottom of the housing and a spacer rib at the underside of the plate, said rib being extended from the plate to a lesser degree than the foot; whereby the corner feet presented by the pads will fit four corners presented by the top of a like housing positioned therebeneath with the rib resting on the top wall of the like housing, while the corner feet alternately serve as a non-slip support when the housing is the bottom one of two like housings stacked one on the other.

2. A housing according to claim 1 where the top wall has a projecting hood extending forwardly beyong the plane of the front panel, said hood having two slots, respectively at the ends thereof, affording corner edges for the two elastomeric feet of a like housing stacked atop.

3. A housing according to claim 1 wherein each foot is a continuous right angle foot and wherein each pad has two spacer ribs.

4. A housing according to claim 2 wherein each foot is a continuous right angle foot and wherein each pad has two spacer ribs.

5. A housing according to claim 1 further comprising a guide upraised from the plate and embracing the corner edges of the housing to which the pad is attached.

6. A box-like surgical accessory housing comprising a top wall, side walls, a bottom wall, a back wall and a front instrument panel having openings therein for instruments employed in the course of surgery, and the four corners at the bottom of the housing each having attached thereto a support pad comprising:
   (a) a plate engaged with the bottom wall;
   (b) a foot downwardly directed from the plate and extending along at least one of the plate edges parallel to the local edges of the bottom wall, the foot being spaced outwardly from the housing so that the corner feet presented by the pads will engagedly fit four edges presented by the top of a like housing positioned therebeneath;
   (c) a spacer rib downwardly directed from the plate but to a lesser extent than that of the foot, the spacer rib being directed so as to lie beneath the bottom wall so that when stacked on top of a like housing positioned therebeneath, the rib rests on the top wall of the like housing; whereas when the housing is the bottom one of the two like housing stacked one on the other, the feet alternately serve as a non-slip support.

7. A housing according to claim 6 wherein the top wall has a projecting hood extending forwardly beyong the plane of the front panel, said hood having two slots, respectively at the ends thereof, affording corner edges for the two feet of the like housing stacked on top.

8. A housing according to claim 7 wherein each foot is a continuous right angle foot which will embracingly engage the corner of the like housing positioned therebeneath and wherein each support pad has two spacer ribs.

9. A housing according to claim 7 wherein each foot is a continuous right angle foot and wherein each support pad has two spacer ribs.

* * * * *